US00PP17115P2

(12) United States Plant Patent
Smittle

(10) Patent No.: US PP17,115 P2
(45) Date of Patent: Sep. 26, 2006

(54) *CANNA* PLANT NAMED 'BALCANYEL'

(50) Latin Name: *Canna×generalis*
Varietal Denomination: Balcanyel

(76) Inventor: Doyle Smittle, 1872 Highway 32, Emmet, AR (US) 71835

( * ) Notice: Subject to any disclaimer, the term of this patent is extended or adjusted under 35 U.S.C. 154(b) by 3 days.

(21) Appl. No.: 11/222,644

(22) Filed: Sep. 9, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—June Hwu
(74) *Attorney, Agent, or Firm*—Audrey Charles

(57) ABSTRACT

A new and distinct cultivar of *Canna×generalis* plant named 'Balcanyel', characterized by its dwarf habit, flowers having bright yellow petaloid staminodia with sparsely scattered red stippling, and dark green slightly glaucous mature foliage.

1 Drawing Sheet

Figure 1:
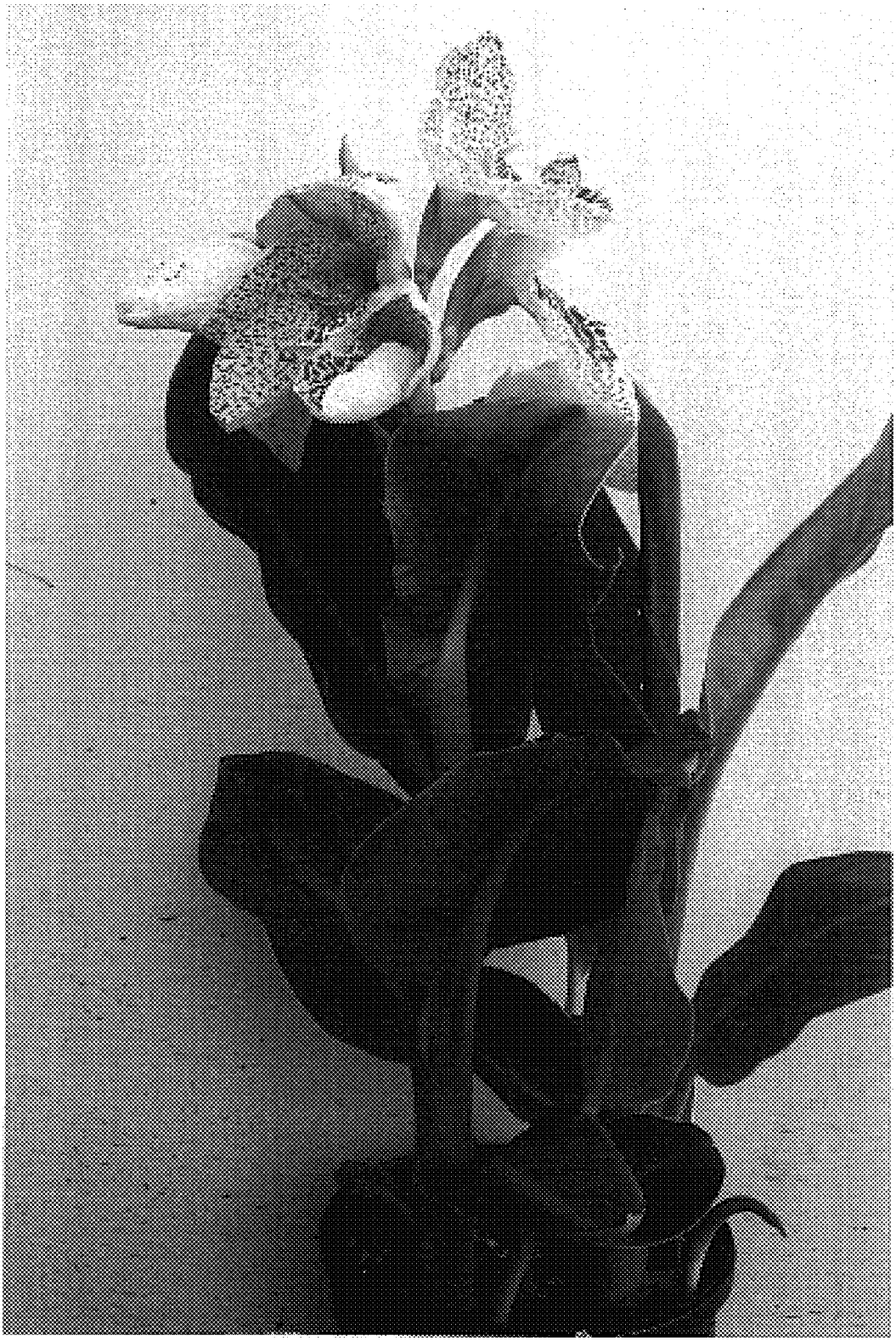

Latin name of the genus and species of the plant claimed: *Canna×generalis*.
Variety denomination: 'Balcanyel'.

BACKGROUND OF THE INVENTION

The present invention relates to a new and distinct cultivar of *Canna*, botanically known as *Canna×generalis*, hereinafter referred to by the name 'Balcanyel'.

The new *Canna* is a product of a planned breeding program conducted by the inventor in Emmet, Ark. The objective of the breeding program is to create new dwarf *Canna* varieties having many large blossoms of various shapes and colors; various foliage colors; and resistance to insect pests. The *Canna* cultivars will bloom prolifically and have self-cleaning blooms.

The new *Canna* originated from a cross made by the inventor in Tifton, Ga. in 2000, of the *Canna×generalis*, cultivar Picasso, a 1.5 to 1.8 m tall plant with green leavews and light yellow, 7.6 cm diameter blooms having densely scattered red stippling on the petaloid staminodia, as the female, or seed, parent. The male parent was *Canna×generalis* cultivar Liberty Yellow, a 0.9 to 1.2 m tall plant, with creamy-yellow, 7.6 cm diameter blooms having sparsely scattered orange stippling on the petaloid staminodia. Neither parent cultivar has been patented.

Compared to plants of the female parent, 'Picasso', the cultivar Balcanyel is dwarf being on average 60 cm tall rather than 1.5 to 1.8 m tall, has dark green slightly glaucous mature foliage rather than green foliage, has three racemes with 15–20 blooms rather than two racemes with 10–15 blooms, and has on average 11.4 cm diameter bright yellow blooms with sparsely scattered red stippling on the petaloid staminodia rather than 7.6 cm light yellow blooms with densely scattered red stippling on the petaloid staminodia. Cultivar Balcanyel sheds the old blooms from the racemes; whereas, the old blossoms of cultivar Picasso are persistent. The cultivar Picasso has severe *Canna* leaf-roller insect damage, but cultivar Balcanyel has only moderate leaf-roller insect damage.

Compared to plants of the male parent, 'Liberty Yellow', the cultivar Balcanyel is dwarf being on average 60 cm tall rather than 0.9 to 1.2 m tall, has dark green slightly glaucous mature foliage rather than green foliage, has three racemes with 15–20 blooms rather than two racemes with 10–15 blooms, has on average 11.4 cm diameter bright yellow blooms rather than 7.6 cm creamy yellow blooms, and has red stippling on the petaloid staminodia rather than orange stippling on the petaloid staminodia. The cultivar Balcanyel is more susceptible to *Canna* leaf-roller as exhibited by moderate damage rather than a slight level of damage for 'Liberty Yellow'.

The cultivar Balcanyel was discovered and selected by the inventor as a flowering plant within the progeny of the stated cross in a controlled environment in Emmet, Ark. The cultivar Balcanyel is perennial to Zone 7.

Asexual reproduction of the new *Canna* by rhizomes in a controlled environment in Emmet, Ark. has shown that the unique features of this new *Canna* are stable and reproduced true to type in successive generations.

SUMMARY OF THE INVENTION

The following traits have been repeatedly observed and are determined to be the unique characteristics of 'Balcanyel'. These characteristics in combination distinguish 'Balcanyel' as a new and distinct cultivar:

1. Dwarf having an average height of 60 cm;
2. Stalks producing three racemes, and each raceme containing a range of 15–20 blooms that are on average 11.4 cm in diameter;
3. Bright yellow petaloid staminodia with sparsely scattered red stippling;
4. Dark green slightly glaucous mature foliage; and
5. Moderately susceptible to *Canna* leaf-roller insect damage.

A preferred comparison plant of the new *Canna* 'Balcanyel' would be the patented cultivar Roblibkey, U.S. Plant Pat. No. 11,129. 'Roblibkey' was reported to be marketed in the United States under the name Liberty™ Keylime; however, the plant appears to be commercially unavailable. In a comparison based on the information in U.S. Plant Pat. No. 11,129, 'Roblibkey' plants have pale yellow with limegreen hue petaloid staminodia while the new *Canna* 'Balcanyel' have bright yellow petaloid staminodia with sparsely scattered red stippling.

Plants of the new *Canna* 'Balcanyel' can be compared to commercially available plants of 'The President', not patented. In side-by-side comparisons conducted in West Chicago, Ill., plants of the new *Canna* 'Balcanyel' differ from plants of 'The President' in the following characteristics:

1. Plants of the new *Canna* 'Balcanyel' are dwarf having an average height of 60 cm compared to an average height of 97 cm for 'The President'; and
2. Plants of the new *Canna* 'Balcanyel' have bright yellow petaloid staminodia with sparsely scattered red stippling compared to solid scarlet red, RHS 42C, petaloid staminodia for 'The President'.

Plants of the new *Canna* 'Balcanyel' can be compared to commercially available plants of 'Rose Futurity', not patented. In side-by-side comparisons conducted in West Chicago, Ill., plants of the new *Canna* 'Balcanyel' differ from plants of 'Rose Futurity' in the following characteristics:

1. Plants of the new *Canna* 'Balcanyel' are dwarf having an average height of 60 cm compared to 73.6 cm for 'Rose Futurity';
2. Plants of the new *Canna* 'Balcanyel' have bright yellow petaloid staminodia with sparsely scattered red stippling compared to solid scarlet red, RHS solid 52B, petaloid staminodia for 'Rose Futurity'; and
3. Plants of the new *Canna* 'Balcanyel' have dark green slightly glaucous mature leaves compared to dark purple, RHS N187A with midvein and leaf edge 187A and core of midvein 194A.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph differ from the color values cited in the detailed botanical description that accurately describe the colors of the new *Canna*.

The photograph comprises a side perspective view of a single flowering plant of 'Balcanyel' grown in a one-gallon container.

DETAILED BOTANICAL DESCRIPTION

The cultivar Balcanyel has not been observed under all possible environmental conditions. The phenotype may vary somewhat with variations in environment and cultural practices such as temperature, light intensity, water status and/or fertilizer rate or type without, however, any variance in genotype.

The photograph and following observations, measurements and values describe plants grown in West Chicago, Ill. with one plant per one-gallon container in polyethylene-covered greenhouses during the winter-spring seasons under conditions which closely approximate commercial production. During the production of the plants, day temperatures ranged from 72–89° F. and night temperatures ranged from 55–65° F. Plants were approximately two months old when the photograph and color values were determined. The chart used in the identification of the colors described herein is The R.H.S. Colour Chart of The Royal Horticultural Society, London, England, 2001 edition. The color values were determined on Jun. 15, 2005 under natural daylight conditions.

Botanical classification: *Canna×generalis* cultivar Balcanyel.

Parentage:

*Female or seed parent.*—'Picasso', not patented.

*Male or pollen parent.*—'Liberty Yellow', not patented.

Propagation:

*Type.*—Rhizome.

*Time to initiate roots.*—About 5 days at temperatures of 72–89° F. days and 55–65° F. nights.

*Time to develop roots.*—About 21 days at temperatures of 72–89° F. days and 55–65° F. nights.

*Rhizome description.*—155A in color covered with papery scale-like leaves of 200N.

*Root description.*—Thick, fibrous 158C in color.

Plant description:

*Plant form and growth habit.*—Erect central stalk with large tropical leaves topped with a colorful inflorescence.

*Branching habit.*—No branching, additional shoots arise from rhizome.

*Plant height.*—Average of 60 cm.

*Plant diameter* (*area of spread*).—39.8 cm.

*Foliage description.*—Arrangement: Simple, alternate. Length: Approximately 24.7 cm, from central stem. Width: Approximately 14 cm. Shape: Ovate, rolled. Apex: Subacute. Base: Aequilateral. Margin: Entire. Texture: Upper surface young foliage: Smooth, glaucous. Texture: Lower surface young foliage: Smooth. Texture: Upper surface mature foliage: Smooth, slightly glaucous. Texture: Lower surface mature foliage: Smooth. Venation pattern: Pinnate. Color: Young foliage, upper surface: closest to 139A. Young foliage, lower surface: Lighter than 139A. Mature foliage, upper surface: closest to 137A, edged with colorless margins. Mature foliage, lower surface: Lighter than 137A. Venation, upper surface: 137B. Venation, lower surface: 137A with a midvein between 145A and 145B. Petiole: Base: Sheathing, overlapping. Texture: Upper (inner) surface: Smooth. Texture: Lower (outer) surface: Smooth, glaucous. Color: Central region 144A fading to lighter 143C at edges.

Flower description:

*Inflorescence arrangement.*—Terminal, indeterminate, racemous.

*Inflorescence appearance.*—Within the inflorescence, flowers borne on short pedicels and occur in pairs composed of two-flowered cincinni.

*Natural flowering season.*—Summer in the north and spring through fall in the south.

*Inflorescence diameter* (*at widest point*).—Approximately 15.8 cm.

*Inflorescence length* (*height from the base of the inflorescence sheath*).—Approximately 24.7 cm.

*Inflorescence sheath.*—Length: Approximately 11.5 cm. Diameter: Approximately 1.7 cm. Texture: Upper (inner) and lower (outer) surfaces: Smooth, glaucous. Color: 144A with colorless edges.

*Flower appearance.*—Each flower is subtended by a bract. The outer whorl of the perianth consists of three, free, imbricate sepals, the inner whorl of three basally united petals. There are four petaloid staminodia constituting the showy portion of the flower with the smaller fertile petaloid stamen and style visible at the center of the flower.

*Flower diameter* (*at widest point*).—Approximately 11.4 cm.

*Flower length* (*height from the base of the pedicel*).—Approximately 8.6 cm.

*Flower bud* (*just before showing color*).—Rate of opening: Approximately 10 days. Length: Approximately 5.6 cm. Diameter: Approximately 0.8 cm. Shape: Gladiate. Color: stippling of 30C overlaid with 16A.

*Bracts.*—Appearance: A single bract subtends the two-flowered cincinni. Length: Approxmately 1.5 cm. Width: 1.2 cm at base to 0.1 cm at tip. Shape: Ovate. Apex: Acute. Margin: Entire. Texture: Upper (inner) and lower (outer) surfaces: Smooth, glaucous. Color: Upper (inner) and lower (outer) surfaces: Translucent 145A fading to colorless at edges.

*Pedicels.*—Length: Approximately 0.5 cm. Diameter: Approximately 0.4 cm. Angle: Acute, about 45 degrees, Strength: Strong. Texture: Rough. Color: 144A.

*Sepals.*—Quantity: Three. Appearance: Free, imbricate. Length: Approximately 1.2 cm. Width: Approximately 0.9 cm. Shape: Ovate. Apex: Acute. Base: Truncate. Margin: Entire. Texture: Upper (inner) and lower (outer) surfaces: Smooth, glaucous. Color: Upper (inner) and lower (outer) surfaces: Translucent 145A fading to colorless at edges.

*Petals.*—Arrangement: Three basally united petals in a whorl. Length: Approximately 4.0 cm. Width: Approximately 1.4 cm. Shape: Navicular. Apex: Acuminate. Base: Truncate. Margin: Entire. Texture: Upper (inner) surface: Smooth, shiny. Texture: Lower (outer) surface: Smooth, glaucous. Color: When opening, upper (inner) and lower (outer) surfaces: Translucent 12B with streaks of 144B. Venation: Colorless. Fully opened, upper (inner) surface: Translucent 13C. Venation: Colorless. Fully opened, lower (outer) surface: Translucent 12C. Venation: Colorless.

*Petaloid staminodia.*—Arrangement: Four overlapping with the innermost highly rolled. Outermost petaloid staminode: Length: Approximately 7.8 cm. Width: Approximately 4.5 cm. Shape: Obovate, concave. Apex: Rounded. Base: Aequilateral. Margin: Entire. Texture: Upper (inner) and lower (outer) surfaces: Smooth. Color: Upper (inner) surface: 11A stippled with 33A. Color: Lower (outer) surface: 12A stippled with 33A at base. Second to outermost petaloid staminode: Length: Approximately 7.5 cm. Width: Approximately 4.9 cm. Shape: Obovate, concave. Apex: Rounded. Base: Aequilateral. Margin: Entire. Texture: Upper (inner) and lower (outer) surfaces: Smooth. Color: Upper (inner) surface: 11A stippled with 33A. Color: Lower (outer) surface: 12A stippled with 33A at base. Third to outermost petaloid staminode: Length: Approximately 8.2 cm. Width: Approximately 5 cm. Shape: Obovate, concave. Apex: Rounded. Base: Aequilateral. Margin: Entire. Texture: Upper (inner) and lower (outer) surfaces: Smooth. Color: Upper (inner) surface: 11A stippled with 33A. Color: Lower (outer) surface: 12A stippled with 33A at base. Fourth to outermost petaloid staminode: Length: Approximately 6.9 cm. Width: Approximately 3.0 cm. Shape: Obovate, rolled under at approximately midway. Apex: Obcordate. Base: Aequilateral. Margin: Entire. Texture: Upper (inner) and lower (outer) surfaces: Smooth. Color: Upper (inner) surface: 12A fading to 12C at edges, stipples of 34A wider and more elongated than on three outermost petaloid staminodia fading to smaller stipples of 33A at base. Color: Lower (outer) surface: 13B stippled with 33A at base.

*Reproductive organs.*—Androecium: Appearance: One, centrally located petaloid stamen, anther fused to inward curved margin. Petaloid stamen: Length: Approximately 6.1 cm. Width: Approximately 1.3 cm. Shape: Falcate, rolled outward at approximately mid-length. Apex: Rounded. Base: Truncate. Margin: Entire. Texture: Upper (inner) and lower (outer) surfaces: Smooth. Color: Upper (inner) surface: 12A fading to 12C at edges, stipples of 34A wider and more elongated than on three outermost petaloid staminodia fading to smaller stipples of 33A at base. Color: Lower (outer) surface: 13B stippled with 33A at base. Anther shape: Elliptic. Anther size: Approximately 1.0 cm by 2.0 mm. Color: Anther at dehiscence: 200A. Pollen amount: Moderate. Color: Pollen: Approximately 159C. Gynoecium: Appearance: One, centrally located petaloid style. Petaloid style: Length: Approximately 6.9 cm. Width at apex: Approximately 0.1 cm. Width at base: Approximately 0.2 cm. Width at widest point: Approximately 0.6 cm. Shape: Ensiform. Apex: Cuneate. Base: Truncate. Margin: Entire. Texture: Upper (inner) and lower (outer) surfaces: Smooth, shiny. Color: Upper (inner) and lower (outer) surfaces: 26A. Style length: Approximately 4.8 cm. Stigma appearance: One, located at tip of petaloid style. Stigma diameter: Approximately 1.0 mm. Color: Stigma: Translucent 11C. Color: Ovary: 144B.

*Seed.*—The cultivar Balcanyel will set seed when exposed to pollinating insects in an outdoor situation. Size: Approximately 8.0 mm. Shape: Round. Texture: Smooth. Color: 200D.

Disease resistance: Resistance to pathogens and pests common to *Canna* has not been observed.

What is claimed is:

1. A new and distinct cultivar of *Canna×generalis* plant named 'Balcanyel', substantially as herein shown and described.

* * * * *